United States Patent [19]

Lind et al.

[11] 4,178,931
[45] Dec. 18, 1979

[54] PORTABLE BIDET, ENEMA AND DOUCHE

[76] Inventors: Gene C. Lind; Ralph C. Lind, both of 3701 Lewis Ave., Long Beach, Calif. 90807; Frank L. Lind, 5958 Gaviota, Long Beach, Calif. 90805; Edmund K. Burchman, 2642 Copa De Oro Dr., Los Alamitos, Calif. 90720; Robert Trauger, 19127 S. Pioneer Space 95, Artesia, Calif. 90701

[21] Appl. No.: 857,228

[22] Filed: Dec. 5, 1977

[51] Int. Cl.² ............................................. A61M 1/00
[52] U.S. Cl. ................................... 128/230; 128/251; 137/355.16; 128/66
[58] Field of Search ............... 128/229, 230, 251, 227, 128/228, 66; 251/84, 85, 176, 186; 137/355.16

[56] References Cited

U.S. PATENT DOCUMENTS

| | | | |
|---|---|---|---|
| 3,085,573 | 4/1963 | Meyer et al. | 128/229 X |
| 3,393,673 | 7/1968 | Mattingly | 128/66 |
| 3,420,228 | 1/1969 | Kalbfeld | 128/66 |
| 3,467,083 | 9/1969 | Mattingly | 128/66 |
| 3,478,774 | 11/1969 | Noakes et al. | 251/176 X |
| 3,495,587 | 2/1970 | Freedman | 128/66 |
| 3,769,977 | 11/1973 | Victory | 128/229 |
| 3,773,046 | 11/1973 | Rosenberg | 128/230 |
| 3,808,608 | 5/1974 | Caplan | 128/229 X |
| 4,078,558 | 3/1978 | Woog et al. | 128/230 X |

FOREIGN PATENT DOCUMENTS 2548580  5/1977  Fed. Rep. of Germany ........... 128/229

*Primary Examiner*—E. H. Eickholt
*Attorney, Agent, or Firm*—I. Michael Bak-Boychuk

[57] ABSTRACT

A portable bidet comprising an electrically driven pump housed on the interior of a split container made in two telescopic halves, the pump including an inlet valve conformed for insertion into the interior of a spring loaded drain opening in one half of the housing. The two halves of the housing are rectangular in shape, the upper half being conformed for telescopic engagement of the lower half to form a cover therefor, the upper half including the above drain opening. When in use the upper half is inverted to form a liquid container supported on the lower half, the spring loaded opening thereof being aligned to engage the input fitting to the pump to be thus opened thereby.

5 Claims, 6 Drawing Figures

U.S. Patent      Dec. 18, 1979      4,178,931
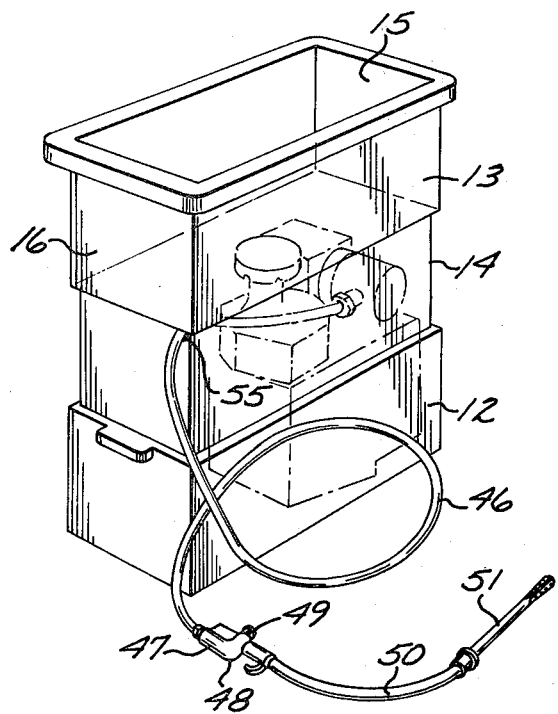
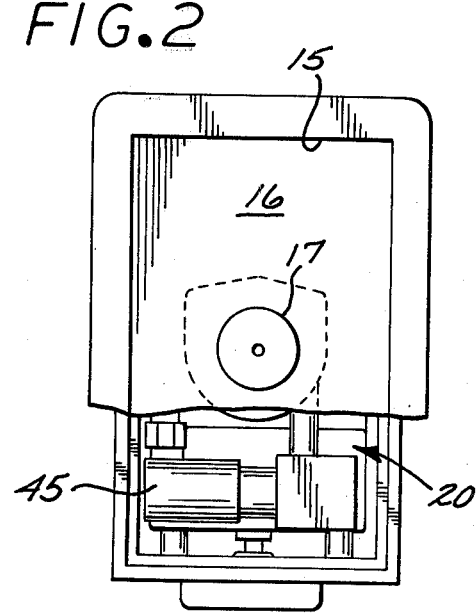
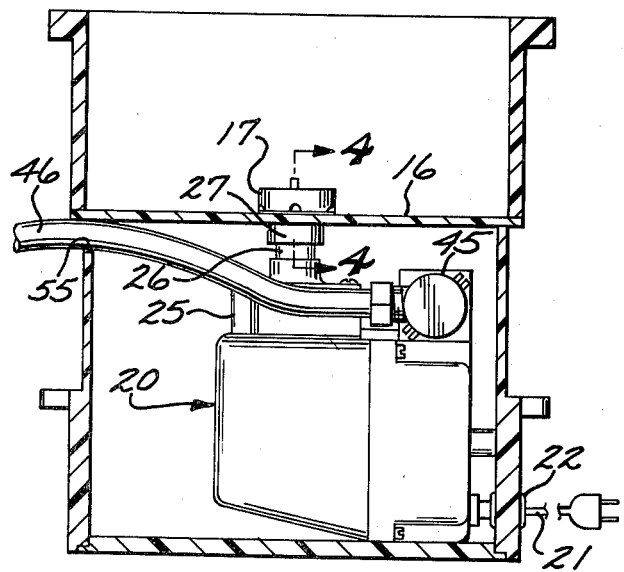
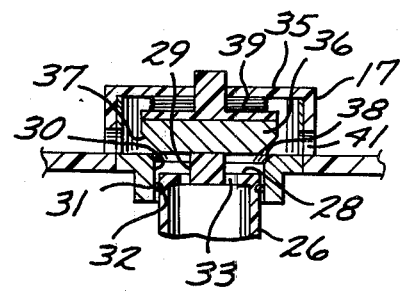
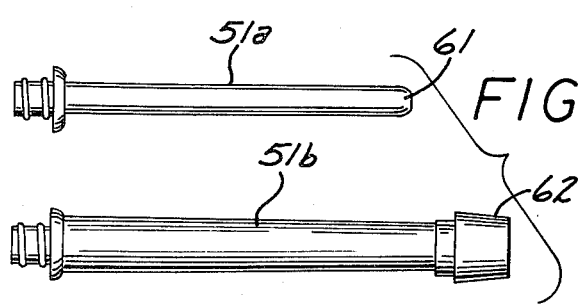
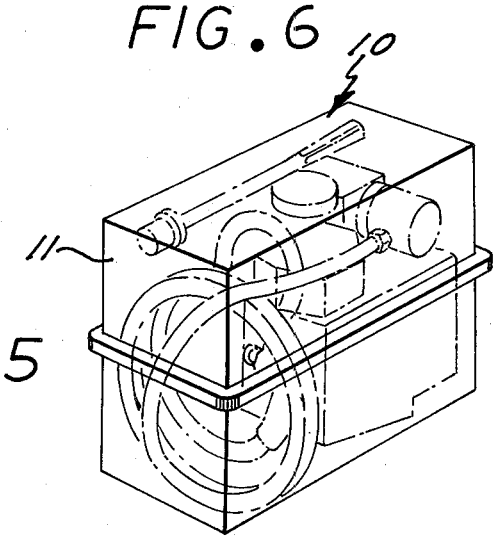

PORTABLE BIDET, ENEMA AND DOUCHE

BACKGROUND OF THE INVENTION

1. Field of the Invention

The present invention relates to cleansing aids and more particularly to sanitary devices adapted for portable use.

2. Description of the Prior Art

A sanitation device like a bidet is quite often not found in many public facilities or facilities providing temporary lodging. Particularly, as mobility and travel options increase, the variations in sanitary implements locally available become continuously greater. For this reason and reasons of convenience there have been various sanitation devices developed in the past which may be used in portable option. Most frequently these sanitation devices comprise passive canisters and therefore rely on gravity in order to perform their function.

As mobility increases the frequency with which sanitation or cleansing is performed away from one's residence also increases. Quite often it is a traveler who, for medical reasons, requires frequent cleansing. Thus the cleansing function is often accompanied by the dispensing of medication and very frequently entails the necessity of dispensing at pressure. The foregoing prior art passive devices often lack the necessary pressure head in order to achieve this desired pressurized dispensing, the necessary pressure levels being frequently found only in stationary or fixed bidets. Of those bidets adapted for portable use the configurations almost in each instance lack the convenience of sealed portability and the convenience of use.

SUMMARY OF THE INVENTION

Accordingly it is the general purpose and object of the present invention to provide a portable sanitation device which is contained in a sealed housing adapted to concurrently function as a container of liquid to be dispensed.

Other objects of the invention are to provide a portable bidet housed in a telescopically closed container, the bidet including an electrically driven pump conformed to ingest fluids from one of the housing halves.

Yet further objects of the invention are to provide a portable sanitation device which is convenient in use, easy to maintain, and requires few parts.

Briefly these and other objects are accomplished within the present invention by providing a thin walled housing assembly including two rectangularly shaped halves, the lower half including a peripheral edge projecting from its opening conformed for telescopic receipt within an upper half. Disposed on the interior of the lower half is an electrically driven pump connected to an input fitting extending to project beyond the plane formed by the peripheral edge. The upper half of the container forms, when inverted, a closed trough which may be utilized to store liquids therein. In order to provide a liquid path from the upper container half into the input fitting, the closing surface of the upper half is provided with a spring-loaded poppet valve conformed to be displaced or unseated by a projection extending from the input fitting. In the alternative mode of assembly the upper half of the container is telescopically advanced over the peripheral edge, the poppet valve including yet another projection to oppose the input fitting. It is this projection that insures a full closure of the poppet valve during transportation. Extending further from the pump is an output fitting terminating in a flexible hose selectively connected to various commercial devices for dispensing the fluids pumped. To provide for manual control over this fluid flow a variable control nozzle is included in the hose. The nozzle itself is provided with a flexible end adapted to receive various insertion instruments as required.

It is contemplated to form the foregoing containers out of a material like plastic the interface therebetween providing a convenient seal in order to contain any residual liquids that may be inadvertently dropped.

BRIEF DESCRIPTION OF THE DRAWINGS

FIG. 1 is a perspective illustration of the inventive device arranged for use;

FIG. 2 is a top view of the device shown in FIG. 1 illustrating the cooperative engagement thereof when in use;

FIG. 3 is a side view in partial section of the device shown in FIG. 2;

FIG. 4 is a detailed view in section of an inventive poppet valve arrangement useful with the device disclosed herein;

FIG. 5 is a side view of various hand fittings useful with the invention disclosed herein; and FIG. 6 is a perspective illustration of the inventive device assembled for transportation.

DESCRIPTION OF THE SPECIFIC EMBODIMENT

As shown in FIGS. 1, 3 and 6 the inventive portable bidet, generally designated by the numeral 10, comprises a rectangular housing 11 including a rectangularly shaped lower half 12 and again a rectangularly shaped upper half 13. Extending along the periphery of the lower half 12 and projecting beyond the opening therein is a rectangular edge surface 14 adapted for receipt within the interior of the upper half 13. The upper half 13 includes an interior cavity 15 again rectangular in plan form and in depth, cavity 15 being conformed to receive the aforementioned peripheral edge 14. Cavity 15 includes a bottom surface 16 provided with a poppet valve assembly 17 substantially central thereto.

Disposed on the interior of the lower half 12 is an electrically driven pump assembly 20 provided with a conventional electrical input lead 21 extending through a grommet 22 inserted into the side of the lower housing half. It is through this input connection power is supplied to the electrically driven pump 20. For the purposes herein any pump available in commerce may be utilized herein.

Formed on the exterior of pump 20 is an input housing 25 terminating in a vertically aligned tube 26 receivable within an input fitting 27 at the free end. As shown in FIG. 4 tube 26 terminates in an end cap 28 closing its free end, cap 28 including a cylindrical projection 29 extending axially beyond the tube. Input fitting 27, in turn, extends from the closing surface of the upper half 13, being directed to the exterior thereof and including a central opening 30 conformed to receive the aforementioned tube 26. In order to provide a sealing interface between tube 26 and the opening 30 an O-ring 31 is deployed within a ring groove 32 formed around the periphery of tube 26, groove 32 being aligned to extend on the interior of the opening 30 when the upper half of the housing 13 is resting in position on the free edge of surface 14. Tube 26 includes a plurality of openings 33 extending through the closing cap 28 disposed around the post or projection 29. Formed on the interior of the cavity 15 and disposed in overlying arrangement over the input fitting 27 is a poppet valve housing 35 securing a poppet valve 36 on the interior thereof. Valve 36 includes a chamfered peripheral edge 37 conformed to engage a chamfered seat 38 on the interior surface of fitting 27. A spring 39, disposed between valve 36 and the housing 35, urges the valve into a seating engagement until displaced by the vertical projection 29. When displaced, the liquids contained in the cavity 15 are free to propagate through a plurality of dispensing openings 41 formed around the periphery of housing 35, the liquids thus draining into the openings 33 and thus through pipe 26 into the interior of pump 20.

Pump 20 furthermore includes an output fitting 45 which may include any conventional pulsing diaphragm, fitting 45 being secured to a flexible hose 46 terminating at the other end in a manually controllable valve assembly 47. More specifically, valve assembly 47 includes a handle structure 48 provided with a trigger 49 which may be variably opened in order to accommodate the desired flow rate. When released, the trigger cuts off all flow. The other end of valve assembly 47 connects to yet another flexible hose 50 which is provided with a threaded fitting to secure to any one of a selected insertion devices shown herein as insertion device 51.

As shown in FIGS. 2 and 6 the disposition of the housing 35 within the closing surface of the upper half 13 is aligned to coincide with the alignment of pipe 26. Thus as the upper housing 13 is inverted, after separation, the placement thereof onto the peripheral edge 14 will concurrently open the poppet valve. In the alternative arrangement the housing half 13 provides a closure for the container 11, that same closure also serving to contain the various insertion devices 51 and the valve assembly 47. In order to permit hose 46 to extend to the exterior of the housing 12 the peripheral edge surface 14 is provided with a semicircular cutout 55 along one edge thereof, cutout 55 being dimensioned to receive the foregoing hose. Upon closure the interior cavity 15 overlies the cutout 55, thus containing the residual fluids from the interior of the container against inadvertent spillage.

As shown in FIG. 5 the foregoing portable bidet may be utilized with various alternative end fitting, fitting 51a and 51b comprising fittings useful in substitution for fitting 51 for performing enema and douche functions. Fitting 51a may include an end opening 61 for providing the function of an enema, while fitting 51b includes an aereator 62 at the end thereof for reducing the impinging mass of the liquid stream therethrough.

Some of the many advantages of the present invention should now be readily apparent. The container 11 may be conveniently cast or manufactured from any plastic material and thus provides an inexpensive structure which both houses the necessary equipment and provides a cavity for mixing cleansing fluids. After use this same container provides a closure against the inadvertent escape of the fluid residue which often includes volatile chemicles with their familiar medication odor. Thus the container may be transported in an inconspicuous form providing both the carrying case as well as the necessary mixing cavity for either cleansing fluid or medication.

Obviously many modifications and variations to the above disclosure can be made without departing from the spirit of the invention. It is therefore intended that the scope of the invention be determined solely on the claims appended hereto.

What is claimed is:
1. A portable cleansing assembly comprising:
   a pump assembly adapted for excitation by a source of A.C. electrical power;
   a first rectangular, hollow container including a rectangular first interior cavity conformed to support said pump assembly, said first container including a planar peripheral surface surrounding said first cavity, the free edge of said surface being conformed to define a plane;
   an input fitting attached to said pump and including an input pipe aligned to extend across said plane defined by said free edge of said peripheral surface, said input pipe includes an end closure formed on the free end thereof, a cylindrical projection extending axially from said end closure and a plurality of bores formed in said end closure in circumferential alignment around said projection;
   a second rectangular hollow container including a second cavity conformed for telescopic receipt of said peripheral surface in a first mode of cooperative alignment and to be supported on said edge in an inverted arrangement in a second mode of cooperative alignment;
   a spring loaded normally closed poppet valve assembly extending across the surface of said second container in receiving alignment with said input pipe when said second container is inverted according to said second mode whereby said poppet valve assembly is unseated by said input pipe, said poppet valve assembly including a valve housing disposed on the interior of said second cavity, a plurality of openings formed in the lateral surfaces of said housing, a through-wall fitting extending from the interior of said housing to the exterior of said second container conformed to receive said input pipe, and a spring-loaded valve urged against said fitting within said housing and deployed for vertical translation by said cylindrical projection;
   output fitting means connected to said pump; and
   liquid dispensing means connected to said output fitting means for dispensing liquids deposited in said second container and transferred through said poppet valve assembly and said pipe.
2. Apparatus according to claim 1 wherein:
   said first and second container are made of plastic.
3. Apparatus according to claim 1 wherein:
   said liquid dispensing means includes a flexible hose connected to said output fitting means and a manually operable valve attached to said hose which automatically cuts off the flow when the pressure is released by the user either voluntarily or involuntarily.
4. Apparatus according to claim 3 wherein:
   said peripheral surface includes a semicircular cutout for passing said hose therethrough.
5. Apparatus according to claim 3 further comprising:
   an end dispenser adapted for operative attachment to said valve for permitting the ejection of said liquids therethrough, said end dispenser including a cylindrical segment terminating in an aereator at the free end thereof.

* * * * *